US012788960B2

(12) United States Patent
Hildebrand et al.

(10) Patent No.: US 12,788,960 B2
(45) Date of Patent: Nov. 10, 2026

(54) INTRAVASCULAR BLOOD PUMPS AND METHODS OF USE

(71) Applicant: SUPIRA MEDICAL, INC., Los Gatos, CA (US)

(72) Inventors: Daniel Hildebrand, Santa Cruz, CA (US); Michael Calomeni, San Jose, CA (US); Gregory M. Hamel, Redwood City, CA (US); Janine Robinson, Half Moon Bay, CA (US); Brian D. Brandt, Morgan Hill, CA (US); Crissly Crisostomo, Santa Cruz, CA (US); Jack Forney, Campbell, CA (US)

(73) Assignee: Supira Medical, Inc., Los Gatos, CA (US)

(*) Notice: Subject to any disclaimer, the term of this patent is extended or adjusted under 35 U.S.C. 154(b) by 580 days.

(21) Appl. No.: 18/248,417

(22) PCT Filed: Oct. 8, 2021

(86) PCT No.: PCT/US2021/054238
§ 371 (c)(1),
(2) Date: Apr. 10, 2023

(87) PCT Pub. No.: WO2022/076862
PCT Pub. Date: Apr. 14, 2022

(65) Prior Publication Data

US 2023/0405298 A1 Dec. 21, 2023

Related U.S. Application Data

(60) Provisional application No. 63/089,184, filed on Oct. 8, 2020.

(51) Int. Cl.
*A61M 60/13* (2021.01)
*A61M 60/855* (2021.01)

(52) U.S. Cl.
CPC .......... *A61M 60/13* (2021.01); *A61M 60/855* (2021.01)

(58) Field of Classification Search
CPC ............................ A61M 60/13; A61M 60/855
See application file for complete search history.

(56) References Cited

U.S. PATENT DOCUMENTS

| | | | |
|---|---|---|---|
| 4,625,712 | A | 12/1986 | Wampler |
| 4,753,221 | A | 6/1988 | Kensey et al. |
| 5,061,256 | A | 10/1991 | Wampler |
| 5,287,858 | A | 2/1994 | Hammerslag et al. |
| 5,507,629 | A | 4/1996 | Jarvik |
| 5,735,892 | A | 4/1998 | Myers et al. |
| 6,007,478 | A | 12/1999 | Siess et al. |

(Continued)

FOREIGN PATENT DOCUMENTS

| | | | |
|---|---|---|---|
| CA | 3014105 | A1 | 8/2017 |
| EP | 3131599 | A1 | 2/2017 |

(Continued)

*Primary Examiner* — Lindsey G Wehrheim
(74) *Attorney, Agent, or Firm* — Shay Glenn LLP

(57) ABSTRACT

Catheter blood pumps that include a collapsible blood conduit, a collapsible scaffold portion, and a bend formed in the collapsible scaffold. The collapsible blood conduit defines a blood lumen. The collapsible scaffold is adapted to provide radial support to the blood conduit. The blood pump also includes one or more impellers.

27 Claims, 5 Drawing Sheets

(56) References Cited

U.S. PATENT DOCUMENTS

| | | | |
|---|---|---|---|
| 6,053,943 | A | 4/2000 | Edwin et al. |
| 6,544,216 | B1 | 4/2003 | Sammler et al. |
| 6,685,696 | B2 | 2/2004 | Fleischhacker et al. |
| 6,712,844 | B2 | 3/2004 | Pacetti |
| 7,022,100 | B1 | 4/2006 | Hosn et al. |
| 7,027,875 | B2 | 4/2006 | Siess et al. |
| 7,220,275 | B2 | 5/2007 | Davidson et al. |
| 7,828,710 | B2 | 11/2010 | Shifflette |
| 8,388,565 | B2 | 3/2013 | Shifflette |
| 8,485,961 | B2 | 7/2013 | Campbell et al. |
| 8,535,211 | B2 | 9/2013 | Campbell et al. |
| 8,591,393 | B2 | 11/2013 | Walters et al. |
| 8,597,170 | B2 | 12/2013 | Walters et al. |
| 8,721,517 | B2 | 5/2014 | Zeng et al. |
| 8,734,508 | B2 | 5/2014 | Hastings et al. |
| 8,814,776 | B2 | 8/2014 | Hastie et al. |
| 8,814,933 | B2 | 8/2014 | Siess |
| 8,849,398 | B2 | 9/2014 | Evans |
| 8,932,141 | B2 | 1/2015 | Liebing |
| 8,934,956 | B2 | 1/2015 | Glenn et al. |
| 9,028,216 | B2 | 5/2015 | Schumacher et al. |
| 9,028,392 | B2 | 5/2015 | Shifflette |
| 9,072,825 | B2 | 7/2015 | Pfeffer et al. |
| 9,138,518 | B2 | 9/2015 | Campbell et al. |
| 9,180,235 | B2 | 11/2015 | Forsell |
| 9,446,179 | B2 | 9/2016 | Keenan et al. |
| 9,512,839 | B2 | 12/2016 | Liebing |
| 9,833,550 | B2 | 12/2017 | Siess |
| 9,872,948 | B2 | 1/2018 | Siess |
| 10,052,419 | B2 | 8/2018 | Er |
| 10,208,763 | B2 | 2/2019 | Schumacher et al. |
| 10,357,598 | B2 | 7/2019 | Aboul-Hosn et al. |
| 10,881,770 | B2 | 1/2021 | Tuval et al. |
| 10,894,115 | B2 | 1/2021 | Pfeffer et al. |
| 11,268,521 | B2 | 3/2022 | Toellner |
| 11,280,345 | B2 | 3/2022 | Bredenbreuker et al. |
| 11,850,413 | B2 | 12/2023 | Zeng et al. |
| 12,017,056 | B2 | 6/2024 | Guo et al. |
| 12,102,815 | B2 | 10/2024 | Dhaliwal et al. |
| 2005/0277803 | A1 | 12/2005 | Pecor |
| 2007/0250148 | A1 | 10/2007 | Perry et al. |
| 2014/0148638 | A1 | 5/2014 | LaRose et al. |
| 2015/0238671 | A1 | 8/2015 | Mesallum |
| 2015/0328382 | A1 | 11/2015 | Corbett et al. |
| 2016/0022890 | A1 | 1/2016 | Schwammenthal et al. |
| 2016/0053763 | A1 | 2/2016 | Toellner |
| 2016/0279310 | A1* | 9/2016 | Scheckel ............. A61M 60/825 |
| 2017/0014562 | A1 | 1/2017 | Liebing |
| 2017/0037860 | A1 | 2/2017 | Toellner |
| 2017/0100527 | A1 | 4/2017 | Schwammenthal et al. |
| 2017/0173242 | A1 | 6/2017 | Anderson et al. |
| 2017/0232169 | A1 | 8/2017 | Muller |
| 2017/0340788 | A1 | 11/2017 | Korakianitis et al. |
| 2018/0080326 | A1 | 3/2018 | Schumacher et al. |
| 2018/0149164 | A1 | 5/2018 | Siess |
| 2018/0303990 | A1 | 10/2018 | Siess et al. |
| 2020/0121835 | A1 | 4/2020 | Farago et al. |
| 2020/0237981 | A1 | 7/2020 | Tuval et al. |
| 2020/0316268 | A1 | 10/2020 | Antoni et al. |
| 2022/0203084 | A1 | 6/2022 | Zarins et al. |

FOREIGN PATENT DOCUMENTS

| | | | |
|---|---|---|---|
| EP | 3153190 | A1 | 4/2017 |
| EP | 3000493 | B1 | 5/2017 |
| WO | WO01/019444 | A1 | 3/2001 |
| WO | WO2015/177793 | A2 | 11/2015 |
| WO | WO2017/210318 | A2 | 12/2017 |
| WO | WO2018/061002 | A1 | 4/2018 |
| WO | WO2018/067410 | A1 | 4/2018 |
| WO | WO2018/078615 | A1 | 5/2018 |
| WO | WO2018/088939 | A1 | 5/2018 |
| WO | WO2018/096531 | A1 | 5/2018 |
| WO | WO2019/191851 | A1 | 9/2019 |
| WO | WO2019/194956 | A1 | 10/2019 |
| WO | WO2019/204689 | A1 | 10/2019 |
| WO | WO2020/028312 | A1 | 2/2020 |
| WO | WO2020/073047 | A1 | 4/2020 |
| WO | WO2020/152611 | A2 | 7/2020 |
| WO | WO2021/062260 | A1 | 4/2021 |
| WO | WO2021/231995 | A1 | 11/2021 |

* cited by examiner

INTRAVASCULAR BLOOD PUMPS AND METHODS OF USE

CROSS REFERENCE TO RELATED APPLICATIONS

This application claims the benefit of U.S. Provisional Application No. 63/089,184, filed Oct. 8, 2020, entitled "INTRAVASCULAR BLOOD PUMPS AND METHODS OF USE", which application is incorporated herein by reference.

This application incorporates the following publications by reference herein in their entireties for all purposes: WO2018/226991; WO2019/094963A1; WO2019/152875A1; WO2020/028537A1; and WO2020/073047A1.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Some intravascular blood pumps may be placed such that at least a portion of the pump, optionally including a pump inflow, is disposed in a left ventricle. Some pump designs, including their size and configuration, may be prone to creating substantial and/or constant contact between a distal region of the pump (optionally an inflow) and a wall of the left ventricle. This may position a pump inflow at a location that increases the likelihood of pulling left ventricular wall tissue towards or into the pump inflow, causing a decrease in pump performance. For example only, this may be important for some pump designs that are relatively long and have straight configurations, and may have distal ends that are more likely to contact a left ventricular wall. Alternatively or additionally, some pumps may be prone to interfering with mitral valve leaflets and/or mitral valve chords with placed in the left ventricle. Additionally, it may be challenging to position some pumps inflows at or within a particular region or location, such as in a region or location within a left ventricle. This disclosure addresses one or more or the above pump design considerations.

SUMMARY OF THE DISCLOSURE

A catheter blood pump is provided comprising a pump portion that includes a collapsible blood conduit configured to be collapsible within a delivery device and expandable to an expanded configuration when deployed from the delivery device, the expanded configuration of the collapsible blood conduit including a blood conduit bend between a blood conduit proximal end and a blood conduit distal end, the collapsible blood conduit including a collapsible scaffold adapted to provide radial support to the collapsible blood conduit, the blood conduit bend including a scaffold bend between a scaffold proximal end and a scaffold distal end, and one or more collapsible impellers at least partially disposed within the collapsible scaffold.

In some embodiments, the collapsible blood conduit includes a central section that includes the blood conduit bend and the scaffold bend.

In one embodiment, the central section includes a midpoint of the scaffold between the scaffold distal and proximal ends.

In some embodiments, a distal section of the blood conduit that is distal to the central section is radially stiffer than the central section.

In one embodiment, a proximal section of the blood conduit that is proximal to the central section is radially stiffer than the central section.

In some examples, the blood pump further comprises a collapsible impeller proximal to the blood conduit bend.

In some examples, the blood pump further comprises a collapsible impeller proximal to the blood conduit bend.

In one example, the scaffold bend includes a bend in a plurality of helical scaffold sections.

A catheter blood pump is also provided comprising a pump portion that includes a collapsible blood conduit configured to be collapsible within a delivery device and expandable to an expanded configuration when deployed from the delivery device, the blood conduit including a bend between a blood conduit proximal end and a blood conduit distal end such that a proximal portion of the collapsible blood conduit is not co-axial with a distal portion of the blood conduit, the collapsible blood conduit including a collapsible scaffold adapted to provide radial support to the collapsible blood conduit, the collapsible scaffold extending through the bend in the collapsible blood conduit, and one or more collapsible impellers at least partially disposed within the collapsible scaffold.

A catheter blood pump is provided comprising a collapsible blood conduit that includes a bend formed therein, and one or more impellers disposed within the collapsible blood conduit.

A catheter blood pump is also provided including any of the features in any combination described herein.

A method of making a pump portion of the catheter blood pump is provided, the method comprising forming a collapsible scaffold that has a configuration adapted to provide radial support to a blood conduit of the pump portion, deforming the scaffold from a first configuration to a bent configuration that includes a bend between a scaffold distal end and a scaffold proximal end, setting the collapsible scaffold in a bent configuration such that the bend is maintained in the scaffold.

In some examples, the method further includes positioning one or collapsible impellers within the collapsible scaffold when it is in the bent configuration.

In some examples, forming the collapsible scaffold comprising laser cutting the scaffold from a tubular member, such as a nitinol tube.

In one embodiment, deforming the scaffold comprising bending the formed scaffold and positioning it in a curved region in a bend forming tool.

In one embodiment, setting the scaffold comprises heat setting the collapsible scaffold in the bent configuration.

In some examples, method further comprises comprising applying a membrane to the scaffold.

In some examples, applying the membrane comprises applying the membrane when the scaffold is in the set bent configuration.

In another example, applying the membrane comprises applying the membrane when the scaffold is in a straightened, non-bent configuration.

In some embodiments, applying the membrane comprises applying the membrane when the scaffold is not in a set configuration.

In other embodiments, applying the membrane comprises applying the membrane to the scaffold when scaffold has less of a bend than in the set configuration.

A method of making a pump portion of the catheter blood pump is further provided, the method comprising forming a straight collapsible scaffold, and bending the collapsible scaffold to a bent configuration.

In some embodiments, bending the collapsible scaffold comprises plastically deforming the straight collapsible scaffold to the bent configuration.

In other embodiments, the method further comprises thermally setting (e.g., heat set) the bent scaffold in the bent configuration.

In some examples, plastically deforming the straight collapsible scaffold to the bent configuration forms and sets the scaffold in an operational expanded bent configuration (e.g., no heat setting is subsequently performed).

A method of sheathing a collapsible pump portion of a catheter blood pump for delivery is provided, comprising deforming a collapsible blood conduit of a pump portion from a bent configuration to a delivery configuration that is straighter than the bent configuration, the collapsible blood conduit comprising a scaffold with a preformed bend, one or more collapsible impellers at least partially disposed within the collapsible scaffold; and positioning the blood conduit within a delivery sheath.

In some examples, the delivery sheath is more rigid than the pump portion such that the increased relative rigidity of the delivery sheath causes the deformation from the bent configuration to the straighter delivery configuration when the pump portion is sheathed (relative axial motion).

A method of positioning a pump portion of a catheter blood pump is provided, comprising delivering a pump portion of a catheter blood pump into a left ventricle within a delivery sheath, the pump portion including a collapsible blood conduit comprising a scaffold with a preformed bend between a blood conduit proximal end and a blood conduit distal end and one or more collapsible impellers at least partially disposed within the collapsible scaffold, deploying the pump portion from a collapsed configuration within the delivery sheath to an expanded configuration.

In some embodiments, the method further comprises positioning the bend within an aortic valve.

In some embodiments, the method further comprises positioning the bend distal to an aortic valve.

In other embodiments, the method further comprises positioning the bend proximal to an aortic valve.

In some embodiments, delivering the pump portion comprising delivering the pump portion in a deformed delivery configuration that is more linear than the expanded configuration with the bend formed therein.

A catheter blood pump is also provided including any of the features herein in any combination.

A method of manufacturing a pump portion of a blood pump is provided, comprising any combination of suitable steps in any suitable order.

A method of making a pump portion of the catheter blood pump is provided, the method comprising coupling a membrane to an expandable scaffold when the scaffold is not in an expanded operational configuration.

A catheter blood pump is provided comprising a pump portion that includes a collapsible blood conduit configured to be collapsible within a delivery device and expandable to an expanded configuration when deployed from the delivery device, the expanded configuration of the collapsible blood conduit including a blood conduit bend between a blood conduit proximal end and a blood conduit distal end, the collapsible blood conduit including a collapsible scaffold adapted to provide radial support to the collapsible blood conduit, the blood conduit bend including a scaffold bend between a scaffold proximal end and a scaffold distal end, and a proximal expandable and collapsible impeller at least partially disposed within the collapsible scaffold, a distal expandable and collapsible impeller at least partially disposed within the collapsible scaffold; and a drive mechanism coupled to the proximal and distal impellers and in rotational communication with the proximal and distal impellers, the drive mechanism extending through the collapsible blood conduit including the blood conduit bend.

In some examples, the drive mechanism includes a bend therein in the region of the collapsible blood conduit bend.

In some embodiments, the drive mechanism and the collapsible blood conduit are and together configured, sized, and adapted, including their bends, to prevent the distal impeller from contacting a distal blood conduit region and the proximal impeller from contacting a proximal blood conduit region.

In other embodiments, the blood conduit bend and the drive mechanism bend having the same or substantially the same compliance.

Any pump portion, wherein the pump portion does not include more than one impeller.

In some examples, the single impeller is distal to a blood conduit set bend.

In another example, the single impeller is proximal to a blood conduit set bend.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The disclosure herein is related to intravascular blood pumps, their methods of use and manufacture. Blood pumps herein may include expandable and/or collapsible blood conduits with a bend formed therein in an expanded configuration. The bend may help position an inflow of the pump portion, while the outflow is disposed in an ascending aorta. For example, a pump inflow may be positioned in a left ventricle outflow tract ("LVOT"), or distal to the LVOT. The bend in the blood conduit may be positioned such that it is at the location of the aortic valve, distal to the aortic valve, or proximal to the aortic valve.

Figure 1:
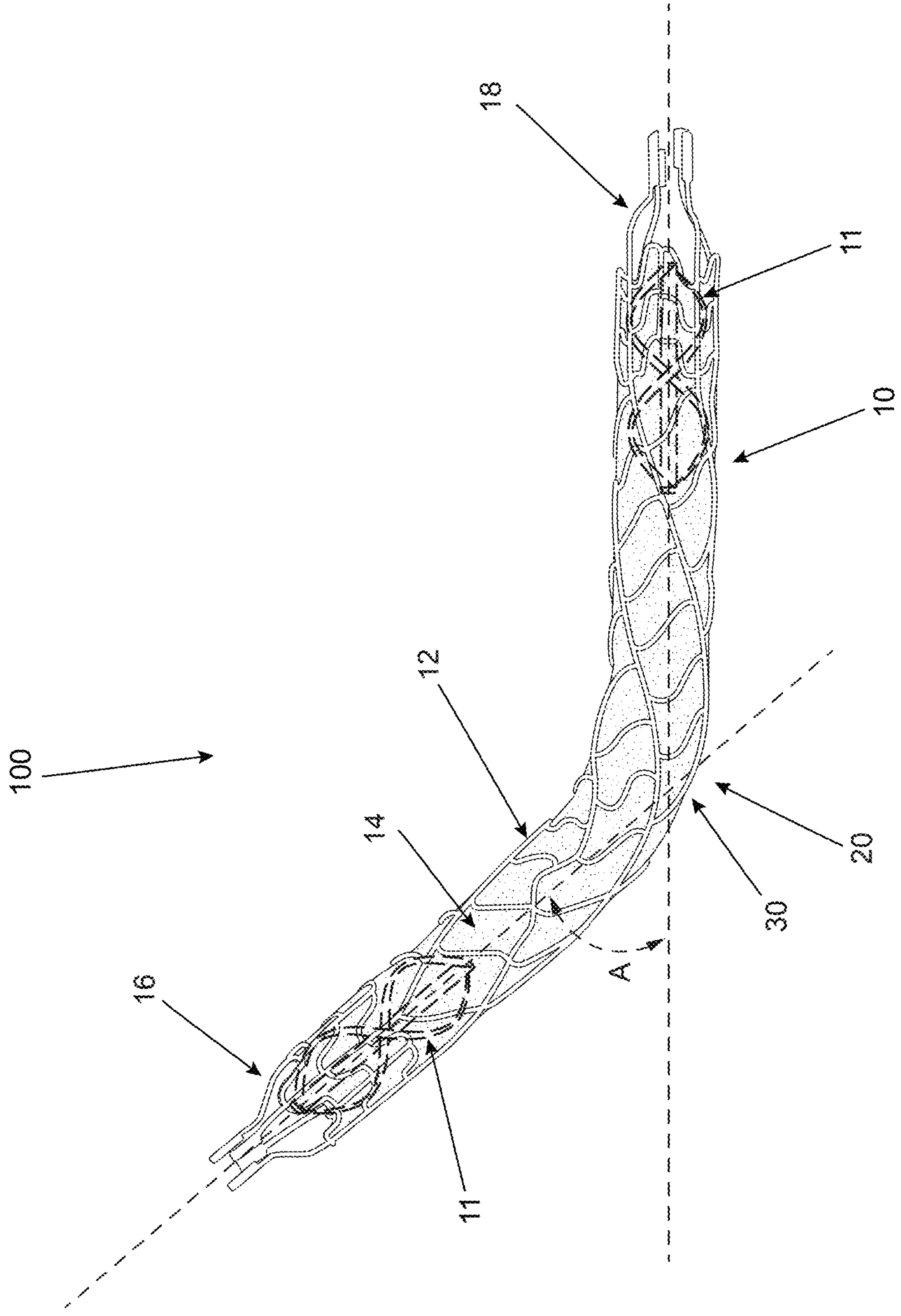
FIG. 1 illustrates a portion of an exemplary pump portion of a catheter blood pump that includes a collapsible blood conduit that includes a collapsible scaffold and a membrane coupled thereto.

FIG. 1 illustrates a portion of an exemplary pump portion of a catheter blood pump 100 that includes exemplary collapsible blood conduit 10 that includes a collapsible scaffold 12 and a membrane 14 coupled thereto. The blood pump can include one or more collapsible impellers 11 disposed within the collapsible scaffold, as shown. For example, the one or more impellers can be disposed at a distal end of the scaffold, at a proximal end of the scaffold, or both. Exemplary collapsible scaffolds 12 may be disposed radially outside of the impeller(s) along the length of the catheter blood pump and may include a bend. The scaffolds can be constructed in a manner and made from materials similar to many types of expandable structures that are known in the medical arts to be able to be collapsed and expanded, examples of which are provided herein. Examples of suitable materials include, but are not limited to, polyurethane, polyurethane elastomers, metallic alloys, etc. The scaffold may be unitary along its length, or it may include non-unitary axially adjacent sections which may include a bend formed therein. Blood conduit 10 includes exemplary proximal struts 16 and distal struts 18, which may be configured as any of the struts herein. While not shown, the pump portion may include one or more collapsible impellers, at least a portion of which are disposed within the collapsible blood conduit 10. A pump portion that includes blood conduit 10 may include any of the impellers herein. The scaffold shown in FIG. 1 is exemplary and any blood conduit herein with a bend formed therein may have any other suitable scaffold configuration. Any of the pumps herein may include a distal impeller in a distal region distal to a bend, a proximal impeller in a proximal region proximal to a bend, or both. The pumps herein may optionally include more than two impellers.

Collapsible blood conduit 10 includes a blood conduit bend 20 formed therein in the expanded configuration, as shown in FIG. 1. The blood conduit bend 20 includes scaffold bend 30 formed in the collapsible scaffold, as shown in FIG. 1. The bend also includes a bend in the membrane material 14 that is coupled to scaffold 12. Membrane 14 may include one or more layers of membrane material. The membrane may be formed with the bend, or the bend may be imparted to the membrane after it is formed or set in a different configuration, examples of which are set forth below.

Bends may be formed and set in a collapsible blood conduit in a variety of ways, and examples provided herein are intended to be illustrative rather than limiting. For example, a scaffold may first be created, such as by laser cutting the scaffold from a tubular member, such as a nitinol tube. In various embodiments, the scaffold may be cut from a tubular material that is sized smaller than the expanded size of the scaffold, or in various embodiments it may be cut from a tubular material that is the same size as the expanded size. In either case, after being cut, the scaffold may have a straight or substantially straight configuration (e.g., tubular).

Figure 2:
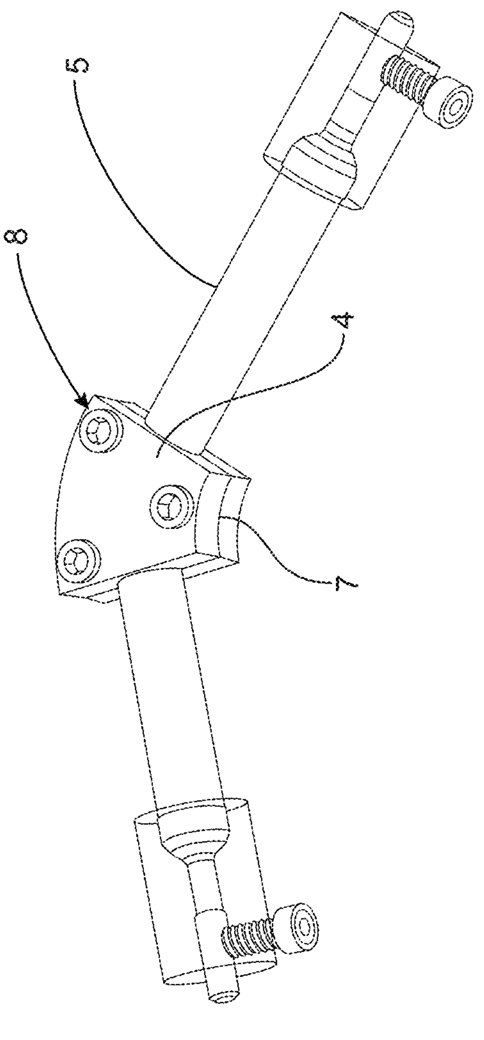
FIG. 2 illustrates a shape set mandrel or shape set assembly configured to form a bend in a scaffold of a blood pump.

In some embodiments, a bend may then be formed and set in the scaffold. For example only, a scaffold 5 (e.g., in the form of an uncut tube as shown, or alternatively as a laser cut scaffold) may be positioned about a shape set mandrel or shape set assembly 4, an example of which is shown in FIG. 2, and thermally treated (e.g., heat set) to set the bend in the scaffold. In some embodiments, the shape set assembly can be clamped or held in place on the scaffold with screws or bolts 8. The assembly can further include a curve 7 corresponding to a curve or angle of the bend that will be imposed into the scaffold after heat treating. Setting the scaffold in the bent configuration causes the scaffold will return to this shape when superelastically deformed, such as when it is unsheathed. The exemplary shape set mandrel or assembly in FIG. 2 includes a bend in a central region that corresponds with the desired scaffold bend angle and bend location. Other bend angles and locations may be imparted to the scaffold by varying the configuration of the shape set mandrel or assembly, examples of which are described herein.

Figure 3:
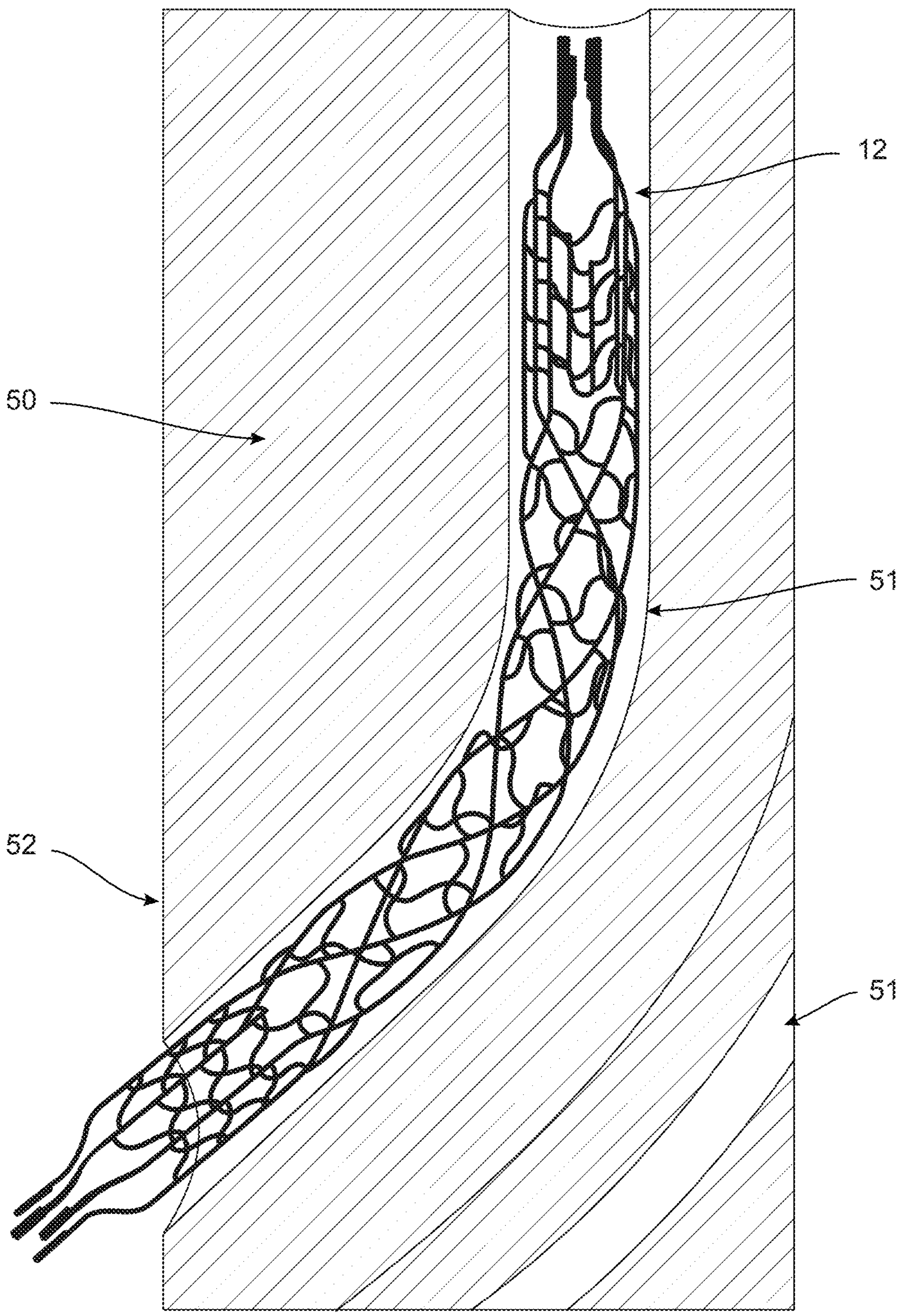
FIG. 3 illustrates an optional verification member in which a set scaffold with a bend may be positioned as shown to assess the scaffold and identify or determine irregularities in the scaffold.

FIG. 3 illustrates a merely optional verification member 50 in which a set scaffold with a bend may be positioned as shown to assess the scaffold and identify or determine irregularities in the scaffold, such as buckling or undesired deformation. As shown in FIG. 3, the verification member 50 can include one or more channels 51 disposed within the verification member and configured to receive a set scaffold. The channel(s) 51 can include the same desired bend at the same desired location within the scaffold to be tested or verified. In some examples, the scaffold can extend beyond an edge 52 of the verification member when the scaffold is placed within the channel, as shown.

Figure 4:
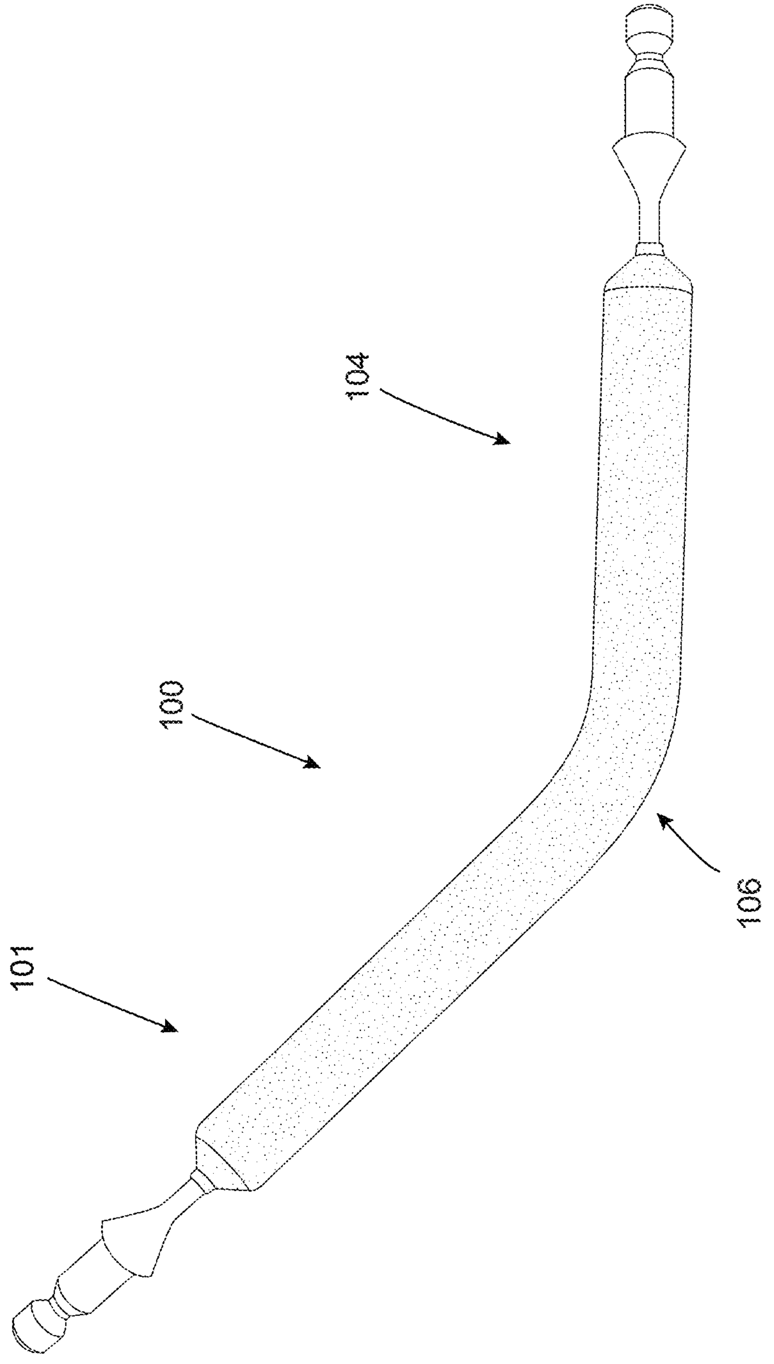
FIG. 4 is an example of a scaffold with a bend positioned on a spray mandrel.

In embodiments in which the scaffold is set in a bent configuration prior to applying a membrane thereto, a membrane may subsequently be applied to the set scaffold in a variety of ways. A merely exemplary step may include positioning the scaffold 100 with a bend 106 set therein on a mandrel (e.g., a spray mandrel), such as exemplary mandrel 101 shown in FIG. 4. Mandrel 101 may have a configuration with a bend therein that corresponds (or is the same as) to the configuration of the scaffold with the bend set therein, as shown. A membrane 104 may then be applied or formed thereon to the bent scaffold while on the mandrel. In some embodiments a membrane is sprayed onto the scaffold and mandrel, and the membrane is allowed to form thereon such that it becomes coupled to the scaffold. The subassembly of scaffold and membrane may be removed from the mandrel.

Any of the membranes herein may be applied to a scaffold at any time during the manufacture of the blood conduit, such as after the scaffold is removed from a thermal treating tool (an example of which is shown in FIG. 2). For example, the scaffold may be removed from a bend setting tool and placed on a mandrel, which may have a straight configuration or which may have a bent configuration that may have the same bent configuration as the bent scaffold. (e.g., FIG. 4). For example only, a membrane may then be sprayed onto the scaffold and allowed to form thereon, becoming coupled thereto.

In any of the embodiments herein, a membrane applied to a scaffold may include more than one layers of material. In some embodiments an inner layer may be applied to the shape set scaffold. For example only, a shape set scaffold may be loaded onto a mandrel that has a membrane layer disposed on the mandrel, such as an extrusion of membrane material laminated on a fluoropolymer or metallic mandrel material. An outer layer may also be applied to the scaffold, such as through a thermal lamination process, or spraying an outer layer onto the scaffold.

In various embodiments herein, a membrane may be dip coated on a shape set scaffold.

In various embodiments herein, a method of manufacturing a shape set blood conduit may include a process that includes stress relieving a membrane that has been previously applied to a scaffold, and in some embodiments may include thermally stress relieving the membrane. The method may further include stress relieving the membrane when the scaffold is in a configuration that is different than a shape set configuration of the scaffold. The method may further include, prior to a stress relief process, initially applying the membrane to the scaffold when the scaffold is in a configuration that is different than the scaffold configuration during the stress relief process.

In various methods that include a membrane stress relief process, a scaffold may have a configuration/shape set therein, such as a shape that includes, for example only, a 60 degree angle (or any other angle). One or more membrane layers may initially be applied to the scaffold when the scaffold has a straight configuration or has a relatively shallow bend, or other configuration for which it may be relatively easy to apply the membrane thereto. The scaffold and membrane subassembly may then be deformed to a configuration with a bend less than (or greater than) the shape set bend of the scaffold, but greater than the angle at which the membrane was applied. For example only, the scaffold and membrane subassembly may then be deformed to include a bend having an angle of 45 degrees. A stress relieving step may then be performed on the membrane, such as a thermal stress relieving step that may include reflowing the membrane when the subassembly is deformed in that configuration, such as by positioning it on a mandrel having the intermediate configuration. This may provide one more exemplary advantages, such as being able to apply the membrane to the scaffold when the scaffold is in a configuration that allows it to be relatively easier to apply the membrane, such as straight or having a relatively shallow bend. Additionally, it may provide stress relief to the membrane when the scaffold is in the shape set configuration. Additionally, it may help keep the membrane taught when the scaffold is the shape set configuration, which may help reduce buckling of the blood conduit lumen, which may interfere with the blood flow therethrough and pump performance. Additionally still, the membrane may have an intermediate unstressed state (in which the angle could also be larger), which may help when sheathing the collapsible blood conduit by reducing sheathing forces and/or help transition the blood conduit from the scaffold set shape towards the intermediate configuration. The blood conduit may be adapted such that the membrane functions as a supportive spring-like element for the collapsible blood conduit in these exemplary embodiments.

In various embodiments, a method could include stress relieving a membrane (e.g., including reflow) when the blood conduit is in a configuration in which the scaffold is in a shape set configuration, such as including a 60 degree bend in the example above.

In various embodiments, a method could include stress relieving a membrane (e.g., including reflow) when the blood conduit is in a configuration in which the scaffold includes a bend with an angle larger than the bend in the shape set configuration, such as including a 75 degree bend in the example above.

One aspect of the disclosure includes methods of manufacturing a collapsible blood conduit that include forming and coupling a membrane to a scaffold when the scaffold is not in a thermally treated (e.g., heat set) configuration.

One aspect of this disclosure includes methods of manufacturing a collapsible blood conduit that include initially applying a membrane to a scaffold, and subsequently thermally relieving stress in the membrane when the membrane is in a different configuration, optionally including a reflow process.

One aspect of the disclosure includes methods of manufacturing a collapsible blood conduit that include creating a collapsible blood conduit, wherein a membrane a scaffold coupled thereto have different unstressed set configurations.

One aspect of this disclosure includes a collapsible blood conduit including a scaffold and a membrane, wherein the scaffold has a thermally treated configuration (e.g., heat set) that is different than an unstressed membrane configuration.

One aspect of this disclosure is a method of manufacture that includes applying a membrane to a formed scaffold when the scaffold is not in a thermally treated configuration (e.g., heat set).

In alternative methods of manufacturing a blood conduit, a bend may first be created in a tubular member, and the scaffold configuration/pattern may subsequently be created after creating the bend. For example, a deformable tubular member may have a bend formed therein, and the scaffold pattern may be subsequently created by laser cutting the bent tubular member. The scaffold may then be thermally treated to heat-set the bend in the scaffold, such as by using a shape set assembly, an example of which is shown in FIG. 2. Any other suitable steps herein may be included in these alternative methods.

One or more impellers and a drive mechanism coupled thereto (an in rotational communication therewith) may be positioned within the blood conduit at any time after the membrane is coupled to the scaffold. In various embodiments, the pump may include two or more impellers inside the scaffold with at least one impeller on either end of the blood conduit bend. Multiple impellers may be off-axis, or not co-axial, such that their axes of rotation are not co-axial.

Referring back to FIG. 1, collapsible blood conduit 10 is an example of a conduit that includes a central section that includes the blood conduit bend and the scaffold bend. The bend may be formed at a midpoint of the blood conduit and a midpoint of the scaffold, the midpoint referring to a midpoint along a length. Collapsible blood conduit 10 is also an example of a conduit having a distal section distal to the central section that is radially stiffer than the central section. The distal section may surround an impeller, which may be a distal impeller. Collapsible blood conduit 10 is also an example of blood conduit with a proximal section proximal to the central section that is radially stiffer than the central section with the bend formed therein. The proximal section may surround an impeller, which may be a proximal impeller. Scaffold 12 is an example of a scaffold with bend 30 that includes a bend in a plurality of helical scaffold sections. In various embodiments, the scaffold in the region of the bend is relatively stiffer than adjacent regions. In various embodiments, the scaffold in the region of the bend is relatively stiffer than the distal and proximal ends of the scaffold.

Collapsible conduit 10 is also an example of a blood conduit in which a proximal region proximal to bend 20 is not co-axial with a distal section that is distal to bend 20, as shown in FIG. 1. In examples that include proximal and distal impellers, the distal and proximal impellers are also not co-axial in the expanded configuration of the blood conduit.

Figure 5:
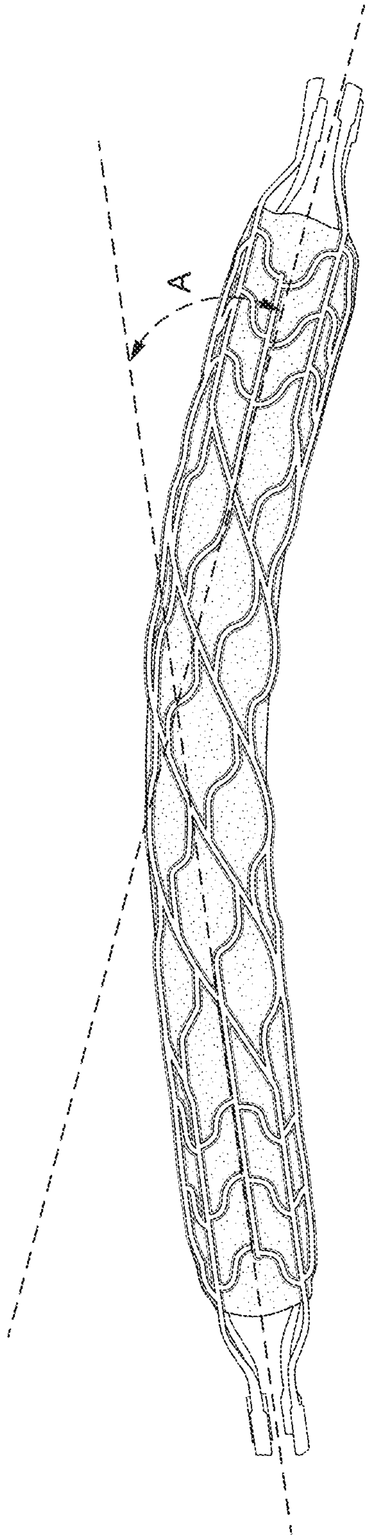
FIG. 5 illustrates an example of a collapsible blood conduit.

Any degree or angle of any of the bends herein may be characterized by an angle between an axis of a region of the blood conduit that is proximal to the bend and an axis of a region of the blood conduit that is distal to the bend and, examples of which are shown in FIGS. 1 and 5, which illustrate angle "A". The angle may be from 1 degree to 80 degrees, such as from 5 degrees to 55 degrees, such as from 10 degrees to 50 degrees, such as from 15 degrees to 45 degrees. The disclosure includes any subrange within any of these ranges as well. In various embodiments, the scaffold includes two or more bends. The bend can be a simple angle or more complex shapes. In various embodiments, the scaffold includes a complex bend with a varying radius or complex shape. As used herein, in various embodiments the angle refers to the overall angle formed by the so-called bend.

FIG. 5 illustrates an exemplary collapsible blood conduit that may have any of the features of blood conduit 10 shown in FIG. 1, and illustrates an exemplary angle A, examples of which are described in more detail herein. In FIG. 5, proximal is to the right in the figure, and distal is to the left, or vice versa.

Methods of manufacturing any of the collapsible blood conduits herein may include forming a collapsible scaffold (e.g., laser cutting a tubular member) that has a configuration to provide radial support to a blood conduit of the pump portion, deforming the scaffold from a first configuration to a bent configuration that includes a bend between a scaffold distal end and a scaffold proximal end, and setting or forming the collapsible scaffold in a bent configuration such that the bend is maintained in the scaffold. A membrane may be applied to the scaffold, such as after the bend is formed and/or after the bend is set. The method may also include positioning one or collapsible impellers within the collapsible scaffold when it is in the bent configuration such that the impellers are not co-axial.

One aspect of the disclosure is a method of sheathing a collapsible pump portion of a catheter blood pump for delivery, the method including deforming a collapsible blood conduit (e.g., conduit 10) from a bent configuration to a delivery configuration that is straighter (optionally completely straight) than the bent configuration. The method may include moving a sheath axially (relative motion) over the conduit to cause its collapse into the collapsed straighter configuration within the sheath. A delivery sheath (e.g., a distal end thereof) is generally more rigid than the collapsible blood conduit (at least in the region of the bend) so that the delivery sheath causes the collapsible blood conduit to straighten from the bent configuration when sheathed. More sheathing force from a delivery sheath may be beneficial on a side or region of the pump that will make more contact with the sheath due to the presence of the bend (e.g., inner curve of bend). Optionally only, a sheath may be made stiffer in one region or side to help facilitate sheathing over the bent portion, and may be relatively less stiff in the other region or side. For example only, a sheath may have a distal end in which an arc of 90, 135, or 180 degrees includes relatively stiffer material (e.g., stiffer polymeric material with higher D) than the remainder of the distal end of the sheath.

One aspect of the disclosure is a method of positioning a pump portion of a catheter blood pump. The method may include delivering a pump portion of a catheter blood pump into a left ventricle within a delivery sheath, deploying the pump portion from a collapsed configuration within the delivery sheath to an expanded configuration with a bend formed therein between a blood conduit (e.g., conduit 10) proximal end and a blood conduit distal end. The method may include positioning the bend within an aortic valve, distal to an aortic valve, or proximal to an aortic valve, while the outflow is in an ascending aorta. Delivering the pump portion may comprise delivering the pump portion in a deformed delivery configuration that is more linear than the expanded configuration with the bend formed therein.

In some embodiments herein, it may be beneficial for a bend region of a collapsible blood conduit to have a stiffness that is similar or the same as a stiffness of a drive mechanism within the blood conduit in the region of the blood conduit bend, whether the blood conduit has a bend set therein or it is passively compliant. For example, the compliance of a drive cable jacket or tubing and/or a drive cable composition may be the same or substantially similar to a compliance of a collapse blood conduit (including a scaffold and membrane) in the region of the blood conduit bend such that when the bend region is deflected, the drive mechanism (including a drive cable) reacts in the same way as the bending shroud. This may prevent contact between rotating components inside the conduit and the inner wall of the blood conduit.

When method steps are described herein, “after,” “before,” “subsequently,” and any other temporal term does not impart a specific time or sequence. For example, use of “after” includes immediately after but is not limited to immediately after unless the disclosure herein indicates otherwise. “After” may be interpreted to mean at some point in time after another step or event.

What is claimed is:

1. A method of making a pump portion of the catheter blood pump, the method comprising:
- forming a collapsible scaffold that has a configuration adapted to provide radial support to a blood conduit of the pump portion;
- deforming the scaffold from a first configuration to a bent configuration that includes a bend between a scaffold distal end and a scaffold proximal end by bending the scaffold and positioning it in a curved region in a bend forming tool;
- setting the collapsible scaffold in a bent configuration such that the bend is maintained in the scaffold.

2. The method of claim 1, further comprising positioning one or collapsible impellers within the collapsible scaffold when it is in the bent configuration.

3. The method of claim 1, wherein forming the collapsible scaffold comprising laser cutting the scaffold from a tubular member, such as a nitinol tube.

4. The method of claim 1, wherein setting the scaffold comprises heat setting the collapsible scaffold in the bent configuration.

5. The method of claim 1, further comprising applying a membrane to the scaffold.

6. The method of claim 5, wherein applying the membrane comprises applying the membrane when the scaffold is in the set bent configuration.

7. The method of claim 5, wherein applying the membrane comprises applying the membrane when the scaffold is in a straightened, non-bent configuration.

8. The method of claim 5, wherein applying the membrane comprises applying the membrane when the scaffold is not in a set configuration.

9. The method of claim 8, wherein applying the membrane comprises applying the membrane to the scaffold when scaffold has less of a bend than in the set configuration.

10. A method of making a pump portion of the catheter blood pump, the method comprising:
- forming a collapsible scaffold that has a configuration adapted to provide radial support to a blood conduit of the pump portion;
- deforming the scaffold from a first configuration to a bent configuration that includes a bend between a scaffold distal end and a scaffold proximal end; and
- heat setting the collapsible scaffold in a bent configuration such that the bend is maintained in the scaffold.

11. The method of claim 10, further comprising positioning one or collapsible impellers within the collapsible scaffold when it is in the bent configuration.

12. The method of claim 10, wherein forming the collapsible scaffold comprising laser cutting the scaffold from a tubular member, such as a nitinol tube.

13. The method of claim 10, wherein deforming the scaffold comprising bending the formed scaffold and positioning it in a curved region in a bend forming tool.

14. The method of claim 10, further comprising applying a membrane to the scaffold.

15. The method of claim 14, wherein applying the membrane comprises applying the membrane when the scaffold is in the set bent configuration.

16. The method of claim 14, wherein applying the membrane comprises applying the membrane when the scaffold is in a straightened, non-bent configuration.

17. The method of claim 14, wherein applying the membrane comprises applying the membrane when the scaffold is not in a set configuration.

18. The method of claim 17, wherein applying the membrane comprises applying the membrane to the scaffold when scaffold has less of a bend than in the set configuration.

19. A method of making a pump portion of the catheter blood pump, the method comprising:

forming a collapsible scaffold that has a configuration adapted to provide radial support to a blood conduit of the pump portion;

deforming the scaffold from a first configuration to a bent configuration that includes a bend between a scaffold distal end and a scaffold proximal end;

setting the collapsible scaffold in a bent configuration such that the bend is maintained in the scaffold; and applying a membrane to the scaffold.

20. The method of claim 19, further comprising positioning one or collapsible impellers within the collapsible scaffold when it is in the bent configuration.

21. The method of claim 19, wherein forming the collapsible scaffold comprising laser cutting the scaffold from a tubular member, such as a nitinol tube.

22. The method of claim 19, wherein deforming the scaffold comprising bending the formed scaffold and positioning it in a curved region in a bend forming tool.

23. The method of claim 19, wherein setting the scaffold comprises heat setting the collapsible scaffold in the bent configuration.

24. The method of claim 23, wherein applying the membrane comprises applying the membrane when the scaffold is not in a set configuration.

25. The method of claim 24, wherein applying the membrane comprises applying the membrane to the scaffold when scaffold has less of a bend than in the set configuration.

26. The method of claim 23, wherein applying the membrane comprises applying the membrane when the scaffold is in the set bent configuration.

27. The method of claim 23, wherein applying the membrane comprises applying the membrane when the scaffold is in a straightened, non-bent configuration.

* * * * *